United States Patent [19]

Ellzy

[11] Patent Number: 5,719,323
[45] Date of Patent: Feb. 17, 1998

[54] METHOD OF MEASURING THE DECOMPOSITION OF A GASEOUS MATERIAL UNDER CONTROLLED TEMPERATURE AND TIME CONDITIONS

[75] Inventor: Michael W. Ellzy, Belair, Md.

[73] Assignee: The United States of America as represented by the Secretary of the Army, Washington, D.C.

[21] Appl. No.: 641,044

[22] Filed: Apr. 12, 1996

[51] Int. Cl.⁶ .................................................. G01N 1/00
[52] U.S. Cl. ................................................ 73/23.41; 73/866
[58] Field of Search .................................. 73/23.41, 23.31, 73/866

[56] References Cited

U.S. PATENT DOCUMENTS

| | | | |
|---|---|---|---|
| 4,407,119 | 10/1983 | Biddle et al. | 60/219 |
| 4,818,348 | 4/1989 | Stetter | 73/866 X |
| 5,266,496 | 11/1993 | Dacruz | 73/23.41 X |
| 5,268,302 | 12/1993 | Rounbehler et al. | 73/23.41 X |
| 5,390,529 | 2/1995 | Ghiselli | 73/23.41 |

*Primary Examiner*—Hezron E. Williams
*Assistant Examiner*—Jay L. Politzer
*Attorney, Agent, or Firm*—Ulysses John Biffoni; Edward L. Stolarun

[57] ABSTRACT

A method and apparatus for measuring the decomposition of a gaseous material under controlled temperature and time conditions. The method is particularly useful for testing the decomposition of pyrotechnic compositions useful in grenades. The method vaporizes the test composition in an enclosed vaporization chamber. Thereafter the process flows a stream of an inert gas into the enclosed vaporization chamber and mixes the vaporized composition with the stream of an inert gas to form a mixed stream. The mixed stream is transferred to an enclosed temperature exposure chamber and exposed to regulated heating conditions for a determined time with subsequent analysis of the exposed mixed stream.

18 Claims, 2 Drawing Sheets

METHOD OF MEASURING THE DECOMPOSITION OF A GASEOUS MATERIAL UNDER CONTROLLED TEMPERATURE AND TIME CONDITIONS

BACKGROUND OF THE INVENTION

1. Field of the Invention

This invention relates to a method and apparatus for measuring the decomposition of a gaseous material under controlled temperature and time conditions. More particularly, the invention relates to a method and apparatus for testing the decomposition of pyrotechnic compositions useful for grenades.

2. Description of the Prior Art

Pyrotechnic grenades are used by both the military and law enforcement agencies for combat and riot control purposes. Grenades usually contain a solid material, which is heated, vaporized and disseminated as a gas or vapor into an environment. The vaporized composition is released to the surrounding area where it condenses to small solid or liquid droplet form intended to be inhaled by the target individual. It is known that the high temperatures and short heating times required for vaporizing cause the decomposition of the compound to some degree, thereby reducing its effectiveness on the target individual. Generally, the amount of decomposition of the components expelled from the grenade in vapor form are unknown until the experimental fabrication of a prototype grenade is completed and the grenade actually tested. It would be desirable to know the degree of decomposition in the early stages of grenade composition development. In this regard, it would be desirable to know the thermal stability of the chemical compound to be disseminated, the minimum and maximum temperatures necessary for material dissemination, the time period of exposure at the minimum and maximum temperatures, the identity of the thermal decomposition products and the degree of thermal and chemical decomposition. The present invention provides a method and apparatus to measure the thermal and chemical decomposition of such pyrotechnic compositions. The composition of interest is vaporized and exposed to a determined temperature for a specific time period. Thereafter the resulting effects of exposure for the given temperature and time are measured and analyzed. This process is repeated for a range of temperatures and times until the composition is fully characterized.

SUMMARY OF THE INVENTION

The invention provides an apparatus for measuring the decomposition products of a composition. It comprises means for vaporizing the composition in an enclosed vaporization chamber, means for flowing a stream of an inert gas into the enclosed vaporization chamber and means for mixing the vaporized composition with the stream of an inert gas to form a mixed stream. Means are provided for transferring the mixed stream to an enclosed temperature exposure chamber and exposing the mixed stream to regulated heating conditions for a determined time. Means are then employed for analyzing the exposed mixed stream.

The invention also provides a method of measuring the decomposition products of a composition by first vaporizing the composition in an enclosed vaporization chamber. Thereafter the process flows a stream of an inert gas into the enclosed vaporization chamber and mixes the vaporized composition with the stream of an inert gas to form a mixed stream. The mixed stream is transferred to an enclosed temperature exposure chamber and exposed to regulated heating conditions for a determined time with subsequent analysis of the exposed mixed stream.

DETAILED DESCRIPTION OF THE PREFERRED EMBODIMENT

Figure 1:
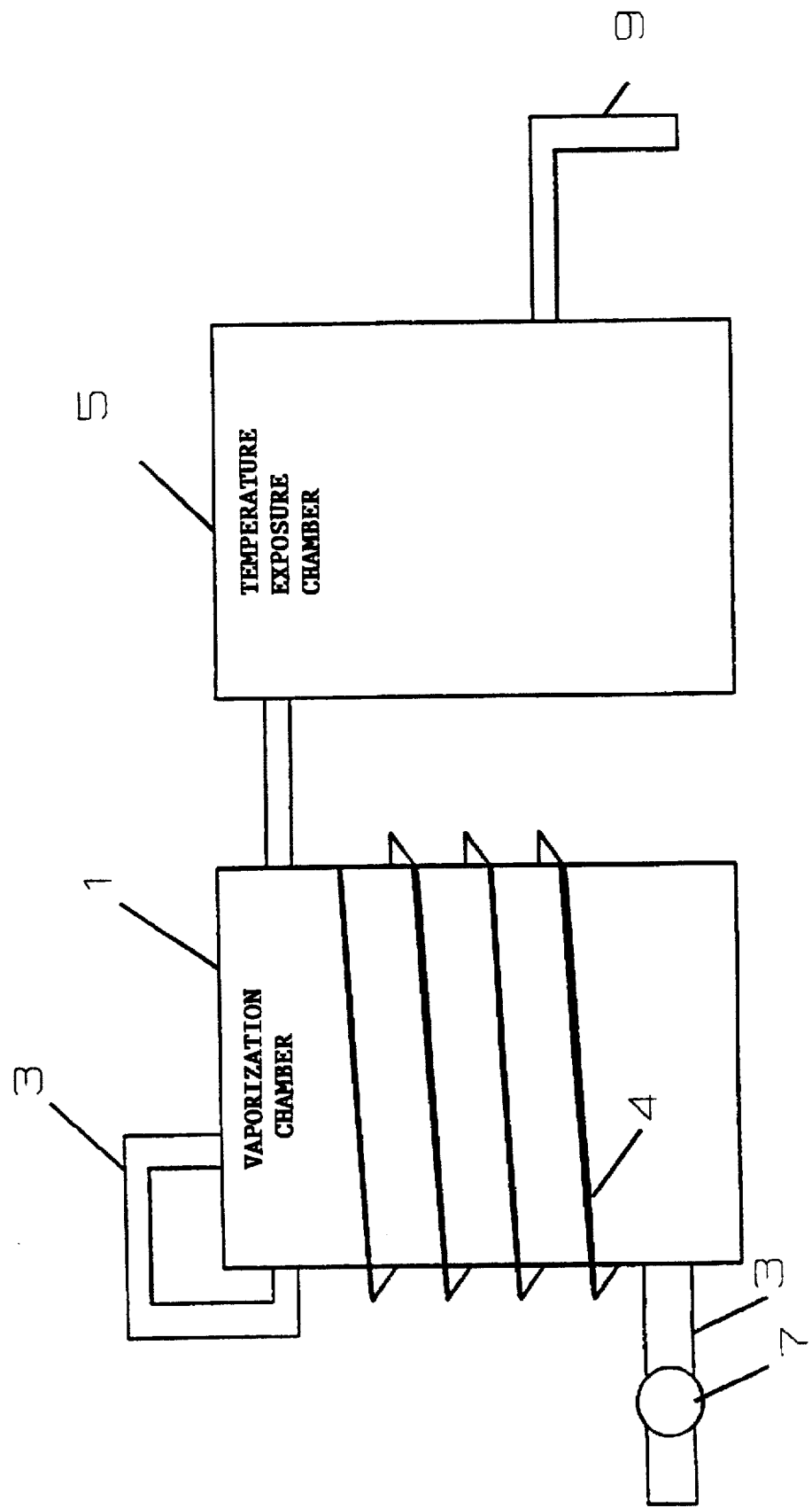
FIG. 1 shows a schematic view of the outside of the apparatus for measuring decomposition of a gaseous material.

FIG. 1 shows an external view of the apparatus. A heated vaporization chamber 1 is used to vaporize a usually solid or liquid chemical composition, such as a pyrotechnic composition, placed in the vaporization chamber to the gaseous state. A controlled amount of an inert carrier gas such as helium, argon, nitrogen or other inert gas flows into the vaporization chamber 1 from a carrier gas flow control inlet 7 to line 3 and copper gas line 4 which surrounds the vaporization chamber. The carrier gas in line 4 is thereby preheated by the heated vaporization chamber 1 and enters the vaporization chamber by line 3 and mixes with the vaporized composition. The vaporized composition is then swept into the temperature exposure chamber 5.

Figure 2:
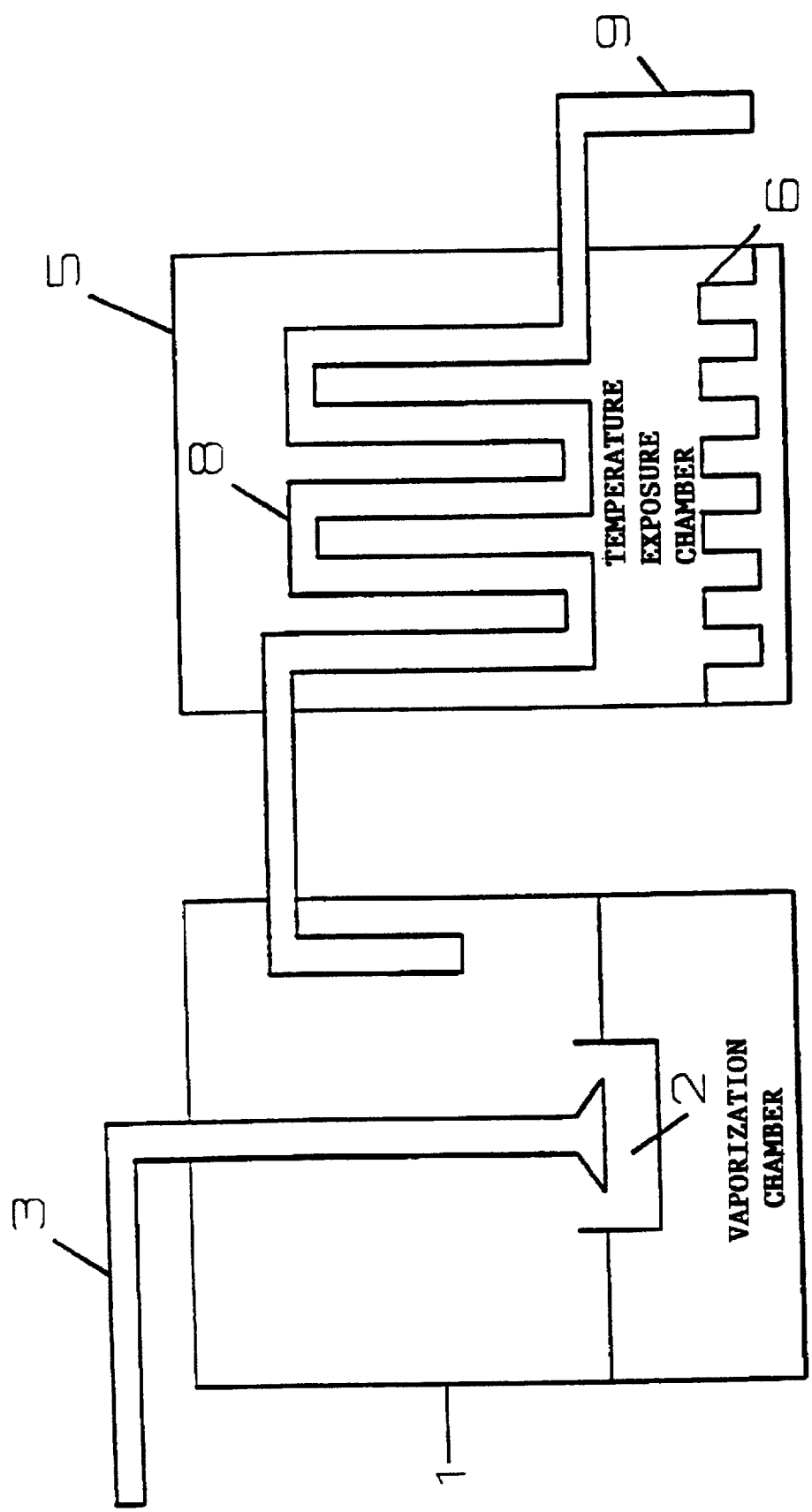
FIG. 2 shows a schematic view of the inside of the apparatus for measuring decomposition of a gaseous material.

As best seen in FIG. 2, the vaporized compound sample 2 mixes with carrier gas from line 3 and the mixture is transferred to the temperature exposure chamber 5 where the vaporized compound is exposed to a preset temperature within a heat conductive tube 8. A heating coil arrangement 6 is located within the exposure chamber 5. The time during which the compound 2 and carrier gas remain in the exposure chamber 5 is controlled by the flow rate of the carrier gas through inlet 7, and the length and diameter of tube 8 in the exposure chamber 5. The exposure time is approximated by the volume of the tube 8 divided by the flow rate. The temperature exposed gaseous mixture is then swept though tube 8, out of the temperature exposure chamber 5 via line 9 and the decomposed composition is analyzed. As a general matter, liquids will vaporize more readily than solids. Preferably, to achieve a sufficient level of vaporization, the vaporizing step is conducted at a temperature of from about 20° C. below the boiling point of liquid compositions to about 100° C. above the boiling point of liquid compositions and for compounds which are solids, from about 20° C. above their melting point to about 20° C. below their boiling or sublimation point at standard temperature and pressure of 25° C. and 1 atmosphere. Accordingly, the need for the application of heat in the vaporization chamber, and the temperature level of any such applied heat, will depend on the choice of the composition or compound to be vaporized and the capability of that composition or compound to generate a suitable amount of vaporization. The decomposed composition may be analyzed by well known chemical analysis techniques such as chromatography and/or spectroscopic techniques such as mass spectroscopy or infrared analysis to analyze the degree of decomposition of the subject composition. The tube 8 may comprise a material such as TEFLON (DuPont trademark for synthetic resin polymer), glass, stainless steel and capillary deactivated fused silica which allow accurate control of the exposure time for the vaporized compound. The exposure time is determined by the flowrate through the length of tubing contained inside the temperature exposure chamber. To increase or decrease the quantity of vaporized compound exposed to a selected temperature the tube diameter inside the temperature exposure chamber is increased or decreased and the tube length may also be varied. Switching tube lengths is accomplished by manually removing a length of tubing and replacing it with a different length. In the preferred embodiment, measurements are made by varying temperatures 1 degree celsius above the compound melting point to a temperature which produces at least 50% decomposition for the specific tube length. Preferably the heating step is conducted at a temperature of from 23° C. to about 400° C. or more preferably from about 100° C. to about 275° C. Preferably the heating step is conducted for from about 0.5 to about 10 minutes or more preferably from about 0.5 to about 2 minutes. In one embodiment, the composition is pyrolyzed in the temperature exposure chamber. Once completed the tube length is replaced and decomposition profile investigated at new lengths and the same temperature range.

Prior art methods for measuring decomposition use systems which must pyrolize the composition in extreme heat to purposely decompose the composition. In these prior types of systems the composition is rapidly heated under vacuum to cause rapid decomposition. Furnaces are required using oxygen depleted atmospheres to cause chemical decomposition. The vaporization and detection process described for this technique has been discussed by Wendandt, W. A., Thermal Analysis 3rd edition, 1986 Chemical Analysis, volume 19. The effluent is swept into an identification analytical instrument for further data collection. The intent of these prior designs is to evaluate the extreme case of maximum decomposition only. The disadvantage of these methods is that they only are applicable to compounds that completely decompose. In contrast, the present invention is able to measure the internal composition changes prior to complete decomposition.

The inventive method and apparatus controls the length of time a compound is exposed to a specific temperature prior to analysis. Heretofore, the determination of the break-down temperature of volatilized compounds as a function of exposure time to varying temperatures could not be ascertained. Prior testing of grenades required the fabrication and actual testing of prototype grenades under field use conditions. Prior systems provide no means of controlling the temperature, flowrate or exposure time of the Volatilized material to the obtained temperature. The present invention achieves this heretofore unobtainable goal of controlling and testing the temperature, flowrate and exposure time of the volatilized pyrotechnic material under a variety of use conditions.

While this invention has been described with reference to the within preferred embodiment and drawings, it is not to be limited thereby, and the invention is to be construed in accordance with the appended claims.

What is claimed is:

1. A method of measuring the decomposition products of a known composition comprising a pyrotechnic material which comprises:

vaporizing the composition in an enclosed vaporization chamber;

flowing a stream of an inert gas into the enclosed vaporization chamber and mixing the vaporized composition with the stream of inert gas to form a mixed stream;

transferring the mixed stream to enclosed temperature exposure chamber and exposing the mixed stream to a regulated heating condition for a determined time to achieve at least some chemical decomposition of the known composition; and analyzing the exposed mixed stream for products of chemical decomposition as a measure of the decomposition of the known composition.

2. The method of claim 1 wherein the inert gas is selected from the group consisting of nitrogen, helium and argon and mixtures thereof.

3. The method of claim 1 wherein the inert gas comprises helium.

4. The method of claim 1 wherein the vaporizing step is conducted at a temperature of from about 20° C. below the boiling point for liquid composition to about 100° C. above the boiling point of liquid compositions and from about 20° C. above their melting point to about 20° C. below their boiling or sublimation point at a temperature of 25° C. and pressure of 1 atmosphere for solid compositions.

5. The method of claim 1 wherein the heating step is conducted at a temperature of from about 23° C. to about 400° C.

6. The method of claim 1 wherein the heating step is conducted for from about 0.5 minutes to about 10 minutes.

7. The method of claim 1 wherein the analyzing of the exposed mixed stream is conducted by one or more techniques selected from the group consisting of chromatography, spectroscopy, mass spectroscopy and infrared analysis.

8. The method of claim 1 wherein vaporizing the composition is conducted at a temperature of from about 1 degree Celsius above the composition melting temperature.

9. The method of claim 1 wherein vaporizing the composition is conducted at a temperature of from about 1 degree Celsius above the composition melting point to a temperature which produces at least 50% decomposition of the composition.

10. The method of claim 1 wherein the composition is pyrolyzed in the temperature exposure chamber.

11. The method of claim 1 wherein the exposing of the mixed stream to a regulated heating condition is controlled by varying the flow rate of the stream of inert gas into the vaporization chamber.

12. A method of measuring the decomposition products of a known composition which comprises:

vaporizing the composition in an enclosed vaporization chamber;

flowing a stream of an inert gas into the enclosed vaporization chamber and the mixing the vaporized composition with the stream of inert gas to form a mixed stream;

transferring the mixed stream to an enclosed temperature exposure chamber and exposing the mixed stream to a regulated heating condition for a determined time to achieve at least some chemical decomposition of the known composition;

analyzing the exposed mixed stream for products of chemical decomposition as a measure of the decomposition of the known composition; and wherein the exposing of the mixed stream to a regulated heating condition for a determined time is conducted by containing the mixed stream in a tube enclosed within the temperature exposure chamber which contains the mixed stream from a point of entry into the temperature exposure chamber to a point of exit from the temperature exposure chamber and to means for analyzing the exposed mixed stream.

13. The method of claim 12 wherein the exposing of the mixed stream to a regulated heating condition is controlled by varying the dimensions of the length and inside diameter of the tube.

14. The method of claim 12 wherein the exposing of the mixed stream to a regulated heating condition is controlled by varying the dimensions of the length and inside diameter of the tube and by varying the flow rate of the stream of inert gas into the vaporization chamber.

15. A method of measuring the decomposition products of a known composition which comprises:

vaporizing the composition in an enclosed vaporization chamber;

flowing a stream of an inert gas into the enclosed vaporization chamber and mixing the vaporized composition with the stream of inert gas to form a mixed stream;

transferring the mixed stream to an enclosed temperature exposure chamber and subjecting the mixed stream to a plurality of different regulated heating conditions in the temperature exposure chamber for a determined time to achieve at least some chemical decomposition of the known composition;

at least one of the plurality of different regulated heating conditions being selected to yield no products of decomposition; and analyzing the exposed mixed stream for products of chemical decomposition for each of the different regulated heating conditions to thereby produce an expanded decomposition profile covering both decomposition and non-decomposition regions of the composition; and wherein the known composition comprises a pyrotechnic material.

16. The method of claim 1 wherein:

the mixed stream is subjected to a plurality of different regulated heating conditions in the temperature exposure chamber; and an analysis for products of decomposition is performed on the mixed stream for each of the different regulated heating conditions to produce a decomposition profile of the composition.

17. The method of claim 16 wherein:

the exposing of the mixed stream to a regulated heating condition is achieved by flowing the mixed stream through a tube contained within the temperature exposure chamber; and the different regulated heating conditions are achieved by flowing the mixed stream through each of a plurality of different tubes, which differ dimensionally from each other.

18. The method of claim 17 wherein:

the tubes differ dimensionally from each other in length and internal diameter.

* * * * *